(12) United States Patent
Ono et al.

(10) Patent No.: US 6,303,157 B1
(45) Date of Patent: Oct. 16, 2001

(54) EXTRACTS OF KAVA-KAVA

(75) Inventors: Mitsunori Ono; Lan Bo Chen, both of Lexington, MA (US)

(73) Assignee: Kava Pharmaceuticals, Inc., DE (US)

( * ) Notice: Subject to any disclaimer, the term of this patent is extended or adjusted under 35 U.S.C. 154(b) by 0 days.

(21) Appl. No.: 09/584,220

(22) Filed: May 31, 2000

(51) Int. Cl.⁷ ............................ A01N 65/00; A61K 35/78
(52) U.S. Cl. ................................................ 424/734
(58) Field of Search ............................................. 424/734

(56) References Cited

U.S. PATENT DOCUMENTS

| | | | |
|---|---|---|---|
| 4,332,825 | 6/1982 | Miyawaki et al. | 426/330.5 |
| 4,727,064 | 2/1988 | Pitha | 514/58 |
| 4,889,634 | 12/1989 | El-Rashidy | 210/646 |
| 5,231,089 | 7/1993 | Bodor | 514/58 |
| 5,296,224 | 3/1994 | Schwabe | 424/195.1 |
| 5,538,721 | 7/1996 | Babcock et al. | 424/78.04 |
| 5,571,534 | 11/1996 | Jalonen et al. | 424/479 |
| 5,679,660 | 10/1997 | Bodley et al. | 514/58 |
| 5,756,484 | 5/1998 | Fuertes et al. | 514/58 |
| 5,997,856 | 12/1999 | Hora et al. | 424/85.2 |

OTHER PUBLICATIONS

Amdidouche–Hussain et al., "Selection of Kavalactones by Complexation of Kava Extract with Cyclodextrins", Drug Development and Industrial Pharmacy 23:1223–1226, 1997.
Lechtenberg et al., "Qualitative and Quantitative Micellar Electrokinetic Chromatography of Kavalactones from Dry Extracts of Piper Methysticum Forst, and Commercial Drugs", Journal of Chromatography 848:457–464, 1999.

Primary Examiner—Herbert J. Lilling
(74) Attorney, Agent, or Firm—Fish & Richardson P.C.

(57) ABSTRACT

This invention relates to a kava-kava lactone-containing product. Also disclosed is a method of preparing such a kava-kava lactone-containing product by extracting kava-kava lactones from crude kava-kava extracts with a solubilizing agent.

23 Claims, 3 Drawing Sheets

EXTRACTS OF KAVA-KAVA

BACKGROUND

The plant kava-kava (piper methysticum Forst. Piperaceae) is native to Polynesia. An intoxicating beverage made from its crushed roots has been used in ceremonies since ancient times.

Kava-kava has been found to have significant analgesic and anesthetic effects via non-opiate pathways. It also can be used as phytotranquilizer to reduce nervousness and overexcitement. However, kava-kava's most popular application is as a natural anxiolytic and has compared favorably to a number prescription medications such as benzodiazepines. Kava-kava's pharmacological activity has been attributed to lactones present in the plant roots.

Several kava-kava products are available, such as kava-kava-based beverages, kava-kava ethanol extract solutions, kava-kava emulsions with glycerin and coconuts oil dispersed in water, and kava-kava extract tablets. Unfortunately, the active lactones in kava-kava-based products have low bioavailability since the lactones themselves are practically insoluble in water. For example, the maximum solubility of kawain at 21° C. is about 2.2 mg/100 ml water. Accordingly, high doses of kava-kava-based products or the active lactones are required to obtain therapeutic effects.

SUMMARY

In one aspect, the invention features a method of obtaining a kava-kava lactone-containing product by heating pulverized kava roots in an aqueous solution which contains a cyclodextrin-based solubilizing agent to extract kava-kava lactones from the pulverized kava-kava roots.

In another aspect, the kava-kava lactone-containing product in dried form includes greater than about 50 parts by weight (e.g., about 50 to about 99 parts by weight) of one or more of the active kava-kava lactones and has a solubility of at least about 0.05 mg/ml (e.g., about 0.05 mg/ml to about 25 mg/ml), preferably greater than about 0.1 mg/ml, and most preferably greater than about 1 mg/ml in water at about 25° C.

The cyclodextrin-based solubilizing agent includes $\alpha$, $\beta$, or $\gamma$ forms of cyclodextrin and derivatives thereof. $\alpha$-cyclodextrin is a ring of six glucose residues, $\beta$-cyclodextrin is a ring of seven glucose residues, and $\gamma$-cyclodextrin is a ring of eight glucose units. Examples of cyclodextrin-based solubilizing agents, include but are not limited to, $\alpha$, $\beta$, or $\gamma$ forms of cyclodextrin, hydroxypropylcyclodextrin, hydroxyethylcyclodextrin, glucosylcyclodextrin, maltosylcyclodextrin, and maltotriosylcyclodextrin. See, for example, U.S. Pat. No. 5,997,856.

In another aspect, the invention features a method of removing flavokawains from a crude kava-kava lactone-containing preparation. The method includes heating the crude kava-kava lactone-containing preparation in an aqueous solution which contains a cyclodextrin-based solubilizing agent to solubilize kava-kava lactones and thereby produce an aqueous kava-kava lactone-containing solution; and removing flavokawains from the solution, such as by filtering. Crude kava-kava lactone-containing preparations, typically, are produced by extracting pulverized kava-kava root with an organic solvent and are commercially available as kava-kava extracts.

In yet another aspect, the invention features a solubilized kava-kava root extract in aqueous form including active kava-kava lactones in a concentration greater than 0.05, preferably greater than about 0.1, and most preferably greater than about 1 weight percent of the extract, and flavokawains in a concentration of less than about 0.3 weight percent of the extract.

In still another aspect, the invention features a solubilized kava-kava root extract in dried form including active kava-kava lactones in a concentration greater than about 50 weight percent of the extract, and flavokawains in a concentration of less than about 0.3 weight percent of extract.

The kava-kava lactone-containing product (i.e., kava-kava root extract) of this invention exhibits desirable composition and performance. It has a high content of kava-kava lactones and a low content of flavokawains, and increased bioavailability and skin permeability of kava-kava lactones when used as an ingredient in a food, pharmaceutical, or cosmetic product.

Other features and advantages of the invention will be apparent from the following detailed description, and from the claims.

DETAILED DESCRIPTION

Figure 1:
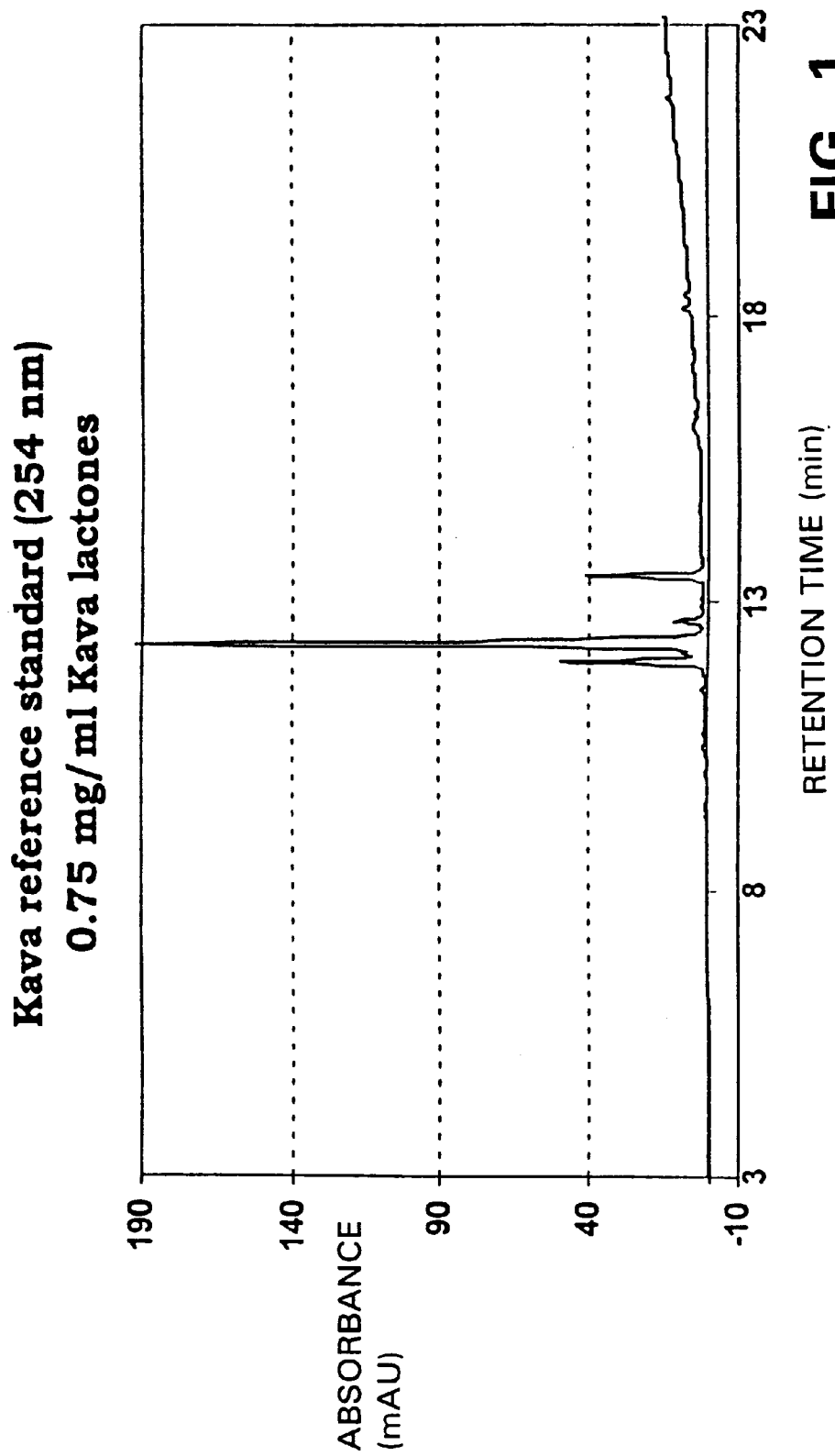
FIG. 1 shows the HPLC spectrum recorded at 254 nm of the major components in a kava-kava lactone-containing product of this invention.

The present invention relates to a kava-kava lactone-containing product which contains one or more active kava-kava lactones complexed with cyclodextrin-based solubilizing agents. The water solubility of active kava-kava lactones complexed with cyclodextrin can be increased by a factor of about 20 relative to the water solubility of the active kava-kava lactones not complexed with the cyclodextrin-based solubilizing agent. The increased water solubility improves the physiological absorption of active kava-kava lactones into the body.

The active lactones in kava-kava are kawain, dihydrokawain, methysticin, dihydromethysticin, yangonin and desmethoxyyangonin, i.e. 6-substituted 4-methoxypryones of the formulae:

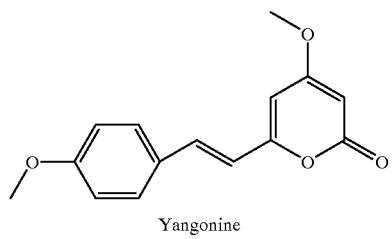

Yangonine

-continued

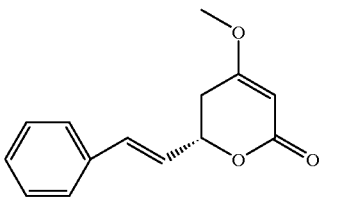

Kawain

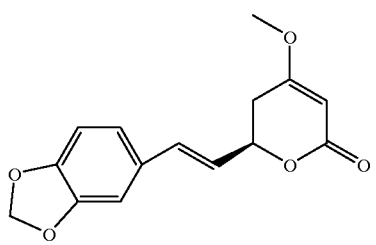

Methysticin

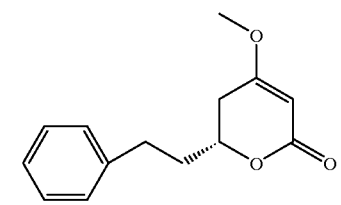

Dihydrokawain

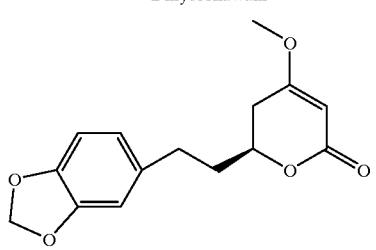

Dihydromethysticin

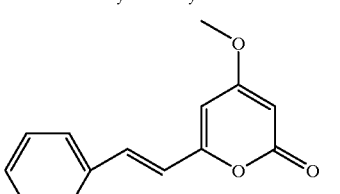

Desmethoxyyangonine

See, for example, Hansel et al., Deutsche Apothekerzeitung 125, No. 41, pages 2056–2058 (1985).

The present invention also relates to a kava-kava lactone-containing product which has reduced amounts of flavokawains of the formula:

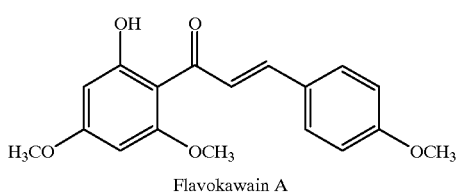

Flavokawain A

-continued

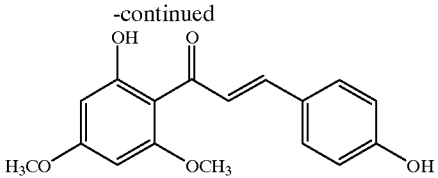

Flavokawain C

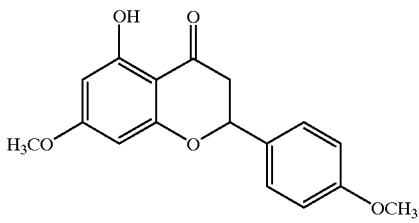

Flavokawain B

Flavokawains are flavone derivatives of the kava-kava active lactone kawain, shown above, and induce undesirable secondary effects such as a scaly skin rash called "Kava dermopathy" when crude kava-kava lactone-containing preparations (e.g., crude kava-kava extracts) are consumed for long-terms or in large amounts. Crude kava-kava lactone-containing preparations, typically, are produced by extracting kava-kava lactones from pulverized kava-kava root with an organic solvent, such as ethanol (ETOH), which also co-extracts flavokawains along with the desired lactones. The kava-kava lactone-containing product of this invention can be taken orally or applied to the skin. In dried form (e.g., a dry solubilized kava-kava root extract), it includes greater than about 50 parts by weight of one or more of the kava-kava lactones and less than about 0.3 weight percent of flavokawains, and has a solubility greater than about 0.05 mg/ml preferably greater than about 0.1 mg/m, and most preferably greater than about 1 mg/ml in water at about 25° C. The kava-kava lactone-containing product, in aqueous form (e.g., an aqueous solubilized kava-kava root extract), includes less than about 0.3 weight percent of flavokawains and kava-kava lactones in a concentration greater than about 0.05, preferably greater than about 0.1, and most preferably greater than about 1 weight percent of the extract. Unexpectedly the method of this invention enables one to extract directly the kava-kava lactones from kava-kava roots without using organic solvents by complexing the kava-kava lactones with a solubilizing agent, e.g., a cyclodextrin-based solubilizing agent.

The cyclodextrin-based solubilizing agent includes α, β, or γ forms of cyclodextrin and chemical derivatives of cyclodextrin. Cyclodextrin can be obtained by reacting starch with a culture liquid of *Bacillus macerans* or with an enzyme liquid formed therefrom, or commercially from, for example, Cyclodextrin Development Inc, located in Gainesville, Fla. Typically, starch is liquefied or gelatinized and reacted with a cyclic oligosaccharide-forming enzyme to form a mixture of cyclodextrins and acyclodextrins. The resulting mixture can be further purified to separate each cyclodextrin.

Cyclodextrin derivatives can be produced by chemically modifying cyclodextrin, e.g., by condensation reactions of cyclodextrins with various epoxides or organic halides. See, for example, Bender et al., "Cyclodextrin Chemistry," Springer-Verlag, Berlin, 1978, pp.29–32. Additionally, electroneutral, soluble cyclodextrin derivatives are described by Parmerter et al. in U.S. Pat. No. 3,453,259 and Gramera et al, in U.S. Pat. No. 3,459,731; cationic, soluble cyclodextrin derivatives are described by Parmerter et al. in U.S. Pat. No. 3,453,257; and insoluble, cross-linked cyclodextrins are described by Solms in U.S. Pat. No. 3,420,788.

Examples of cyclodextrin-based solubilizing agents, include but are not limited to, α, β or γ forms of cyclodextrin, hydroxypropylcyclodextrin, hydroxyethylcyclodextrin, glucosylcyclodextrin, maltosylcyclodextrin, and maltotriosylcyclodextrin. See, for example, U.S. Pat. No. 5,997,856. Preferably, the cyclodextrin-based solubilizing agent is hydroxypropylcyclodextrin. Typically, β-cyclodextrin-based solubilizing agents such as β-cyclodextrin, β-hydroxypropylcyclodextrin, β-hydroxyethylcyclodextrin, β-glucosylcyclodextrin, β-maltosylcyclodextrin, or β-maltotriosylcyclodextrin are preferred. β-hydroxypropylcyclodextrin (e.g., hydroxyproply-beta-cyclodextrin) is particularly preferred.

The method of preparing a kava-kava lactone-containing product includes mixing between about 1 and about 20 parts by weight of a crude kava-kava extract or pulverized kava-kava root with about 100 parts by weight of a solution heated to between about 30° C. and about 70° C. of water containing about 0.01 to about 25 percent by weight, and preferably about 0.1 to about 15 percent by weight of the cyclodextrin-based solubilizing agent relative to the total weight of the aqueous solution. The resulting mixture is heated to about 50° C. to about 90° C. and stirred for about 1 to about 10 minutes. While stirring, the mixture is cooled to about 30° C. to about 50° C. for between about 1 and about 10 minutes. The supernatant contains water-soluble complexes of active kava-kava lactones and cyclodextrin-based solubilizing agents.

Unexpectedly, cyclodextrin-based solubilizing agents have relatively weak affinity for forming a water-soluble complex with flavokawains as compared to kava-kava lactones. As a result most of the flavokawains in the kava-kava crude extract or pulverized kava-kava root are not solubilized into the supernatant. Residual amounts of flavokawains in the supernatant, e.g., about 3% to about 0.5%, give rise to a yellow color of the supernatant and can be removed by microfiltering the supernatant. The microfiltered supernatant is colorless and substantially flavokawain-free. Any microfilter having a pore size sufficient to remove residual flavokawain (e.g., 1 μm) can be used. In alternative embodiments, residual amounts of flavokawains in the supernatant can be removed by cold precipitation or solvent distribution.

The kava-kava lactone-containing product of this invention can be produced by a batch method or a flow method, i.e., a continuous extraction and filtration process. Typically, flow processes are used to help maintain reasonable manufacturing costs. The kava-kava lactone-containing product in aqueous form can be dried, (e.g., under vacuum) to produce a dried product. The kava-kava lactone-containing product, either in dried or aqueous form, can be incorporated into an edible composition, pharmaceutical composition, a cosmetic product, or a skin care product. The edible composition can be a solid, a paste, or a liquid food product, such as water, milk, tea, coffee, soft drinks, juices, beer, seasonings, cereals, cookies, chewing gum, chocolate, or soups.

Without further elaboration, it is believed that the above description has adequately enabled the present invention. The following specific examples are, therefore, to be construed as merely illustrative, and not limitative of the remainder of the disclosure in any way whatsoever. All of the publications cited herein, including patents, are hereby incorporated by reference in their entirety.

EXAMPLE 1

50 g of a crude kava-kava extract containing about 7.5 g of kava-kava lactones and about 3 weight percent flavokawains. (i.e., alcohol free KAVA-KAVA root suspension manufactured by Nature Answer Inc., Hauppauge, N.Y.) was added to 3 liters of hot water containing 200 g of hydroxypropyl beta cyclodextrin (Trappsol manufactured by Cyclodextrin Development Inc, Gainesville, Fla.) at 70° C. The mixture was stirred at 90° C. for 10 minutes and then at 50° C. for an additional 10 minutes. The supernatant was filtered through a 1 μm-pore size microfilter to yield 3.3 liters of a visibly colorless and clear water-soluble kava-kava lactone-containing solution. The kava-kava lactone content of the solution was about 1.6 mg/ml. The concentration of flavokawains was less than about 0.3 weight percent.

EXAMPLE 2

50 g of a crude kava-kava extract containing about 7.5 g of kava-kava lactones extracted with EtOH and about 3 weight percent flavokawains ( i.e., KAVA-KAVA Root GBE ethanol solution manufactured by GAIA Herbs Inc, Brevard, N.C.) was added to 3 liters of hot water containing 300 g of hydroxypropyl beta cyclodextrin (Encapsin HPB manufactured by American Maize-Products Company, Hammond, Id.) at 70° C. The mixture was stirred at 90° C. for 10 minutes. Residual EtOH was removed from the mixture by evaporation under vacuum at 30° C. The supernatant was filtered through a 1 μm-pore size microfilter to yield 3.2 liters of a visibly colorless and clear water-soluble (alcohol-free) kava-kava lactone-containing solution. The kava-kava lactone content of the solution was about 2.0 mg/ml. The concentration of flavokawains was less than about 0.3 weight percent.

EXAMPLE 3

50 g of a crude kava-kava extract containing about 7.5 g of kava-kava lactones and about 3 weight percent flavokawains (i.e., KAVA-KAVA Root GBE ethanol solution manufactured by GAIA Herbs Inc, Brevard, N.C.) was added to 3 liters of hot water containing 20 g of β-cyclodextrin (C*Cavitron 82800, food grade, manufactured by Cerester USA Inc in Hammon, Ind. The mixture was stirred at 90° C. for 10 minutes and then at 50° C. for an additional 10 minutes. The supernatant was filtered through a 1 μm-pore size microfilter to yield 3.0 liters of a visibly colorless and clear water-soluble kava-kava lactone-containing solution. The kava-kava lactone content of the solution was about 0.25 mg/ml. The concentration of flavokawains was less than about 0.3 weight percent.

EXAMPLE 4

50 g of a crude kava-kava extract containing about 5 g of kava-kava lactones extracted with EtOH and about 3 weight percent flavokawains (i.e., KAVA-KAVA Root GBE ethanol solution manufactured by GAIA Herbs Inc, Brevard, N.C.) was added to 3 liters of hot water containing 20 g of cyclodextrin and 150 g of hydroxypropyl beta cyclodextrin at 70° C. The mixture was stirred at 90° C. for 10 minutes and then at 50° C. for an additional 10 minutes. The supernatant was filtered through a 1 μm-pore size microfilter to yield 2.8 liters a visibly colorless and clear water-soluble kava-kava lactone-containing solution. The kava-kava lactone content of the solution was about 1.2 mg/ml. The concentration of flavokawains was less than about 0.3 weight percent.

EXAMPLE 5

A crude kava-kava extract containing 75 mg kava-kava lactones perl ml ethanol and about 3 weight percent flavokawains (KAVA-KAVA Root GBE manufactured by GAIA Herbs Inc, Brevard, N.C.) was used to prepare a reference standard for high-pressure liquid chromatography (HPLC) measurements. More specifically, 1 ml of the standardized kava-kava extract was added to 9 ml of water containing 1 g of hydroxypropyl beta cyclodextrin (USP grade) at 50° C. The mixture was stirred for 5 minutes to yield a standardized kava-kava extract solution (yellowish). An HPLC sample was prepared by diluting it with 5× of 80% EtOH. The concentration of flavokawains in the sample was about 3 weight percent.

Figure 2:
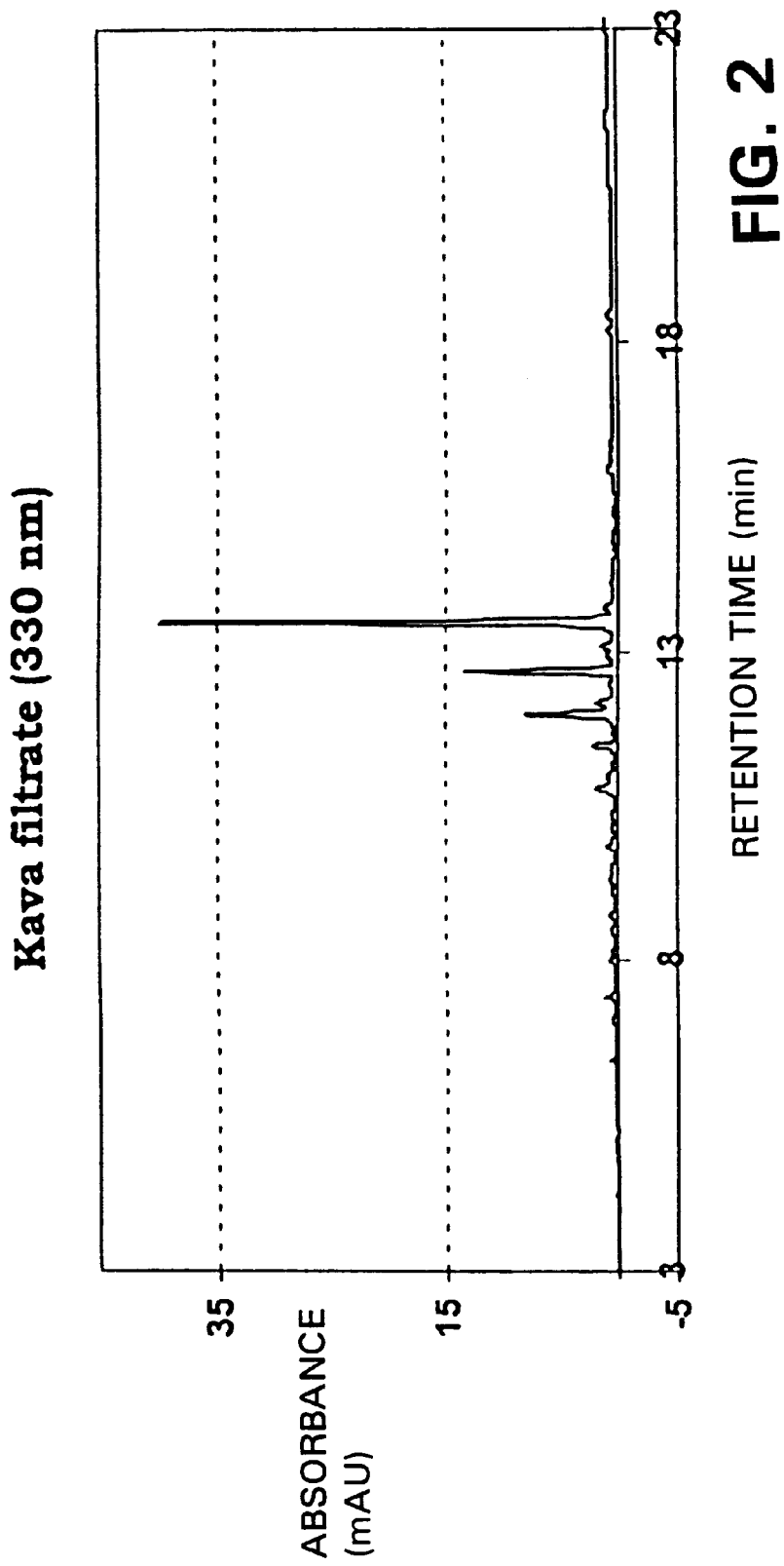
FIG. 2 shows the HPLC spectrum recorded at 330 nm of the major components in the same product used to record the HPLC spectrum of FIG. 1.
Figure 3:
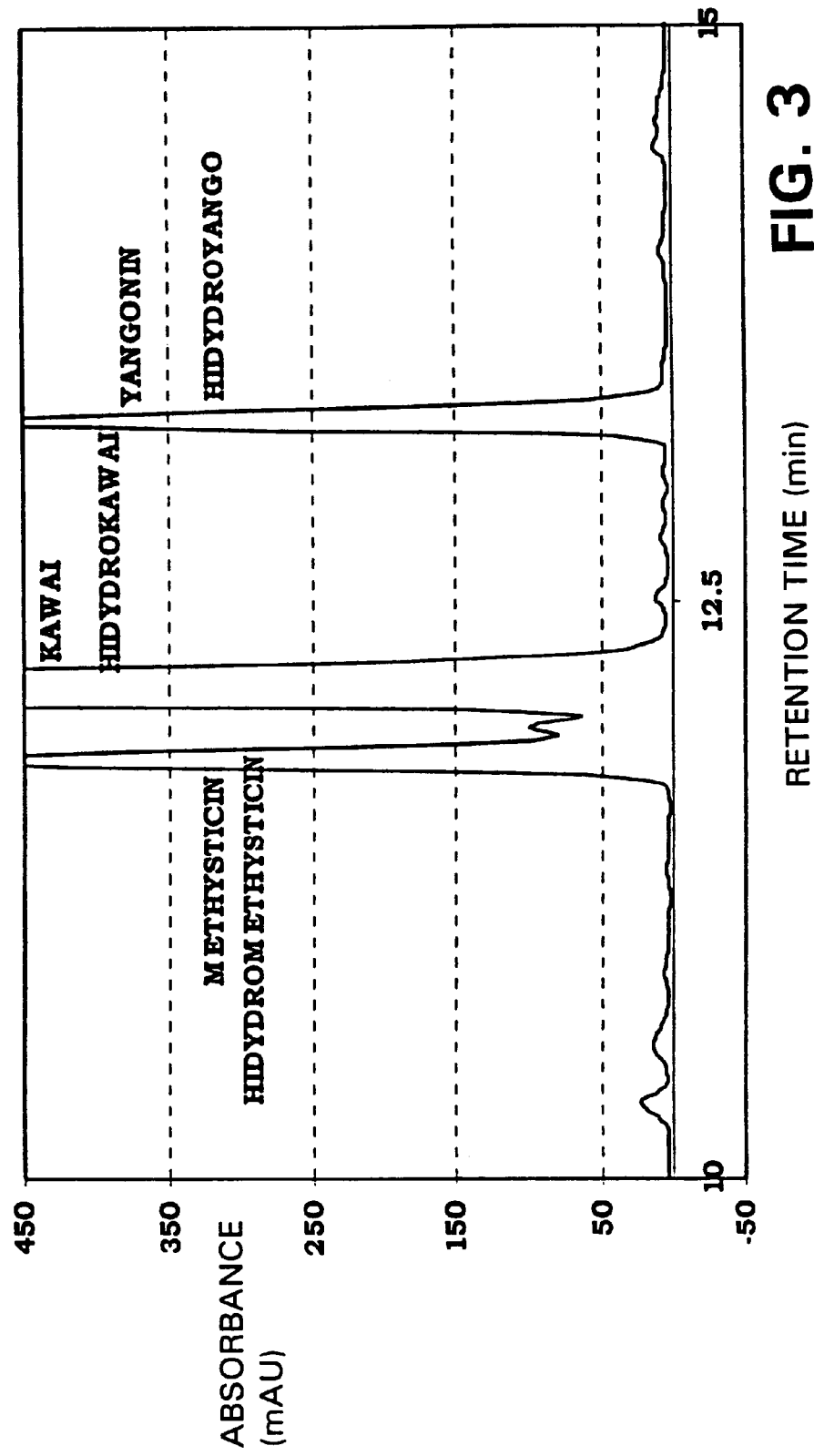
FIG. 3 shows an expanded view of the HPLC spectrum of FIG. 1.

HPLC spectra were recorded on a HP 1050 instrument (Hewlet Packard) using a C18-reverse phase column 150 mm×4.6 mm, Symmetry Shield RP18 available from (Waters) by a gradient elution method, i.e., 1 ml/min for 20 minutes with 20%–95% aqueous acetonitrile and 0.1% trifluoroacetic acid at 30° C. The HPLC detector was set at either 254 nm or 330 nm. FIG. 1 shows the HPLC spectrum of the standardized kava-kava extract solution recorded by monitoring the absorption at 254 nm as a function of time. FIG. 2 shows a HPLC spectrum of the standardized kava-kava extract solution recorded by monitoring the absorption at 330 nm as a function of time. The six kava-kava lactones appear in the HPLC spectra of FIGS. 1 and 2 as overlapping peaks (FIG. 3) Note that the intensity of each absorbance is not directly related to the relative amounts of kava lactones in the standardized Kava extract because each lactone has a different absorption maxima ($\lambda$max) value and extinction coefficient.

EXAMPLE 6

Flavokawains have a maximum absorption around about 340 nm and are responsible for the yellow color of the standardized kava-kava extract solution. The flavokawian's (i.e., the yellowish color) in the HPLC sample of Example 5 were removed from the solution by filtering it with through a 0.45 um microfilter. The concentration of flavokawains in the filtered HPLC sample was less than about 0.3 weight percent.

EXAMPLE 7

200 g of pulverized dry kava-kava root, available from Drinks That Work Ltd., Santa Cruz, Calif., was added to 2.5 liters of hot water containing 250 g of hydroxypropyl beta cyclodextrin (Trappsol manufactured by Cyclodextrin Development Inc, Gainesville, Fla.) at 70° C. The mixture was stirred at 80° C. for 10 minutes and the supernatant was separated from the pulverized kava root residue under suction filtration. The kava-kava root residue was extracted with another 2.5 liters of hot water containing 250 g of hydroxypropyl beta cyclodextrin (Trappsol) under the same conditions of the previous extraction. After suction filtration, the two supernatants were combined and then filtered through Celite bed filter paper under vacuum to yield 4.9 liters of a clear yellow solution.

EXAMPLE 8

200 g of pulverized dry kava-kava root, available from Drinks That Work Ltd., located in Santa Cruz, Calif., was added to 2.5 liters hot water containing 25 g of beta cyclodextrin (Trappsol) (manufactured by Cyclodextrin Development Inc, Gainesville Fla.) at 70° C. The mixture was stirred at 80° C. for 10 minutes and the supernatant separated from the pulverized kava root residue under suction filtration. The kava-kava root residue was extracted with another 2.5 liters of hot water containing 25 g of beta cyclodextrin (Trappsol) under the same conditions of the previous extraction. After suction filtration, the two supernatants were combined and then filtered through Celite bed filter paper filter under vacuum to yield 4.9 liters of a clear yellow solution.

EXAMPLE 9

The kava-kava lactone content of each of the solutions obtained from Examples 7 and 8 was determined by adding about 100 ml of water to the solution to bring its total volume to about 5.0 liters. A 0.5 ml aliquot from each solution was mixed with 0.5 ml EtOH and centrifuged (Centrifuge 5415C, manufactured by Eppendorf) with 1.4× 1000 min$^{-1}$ for 5 minutes. After centrifugation, the supernatant was filtered through a 0.45 $\mu$m microfilter and a 5 $\mu$l aliquot of the filtered solution was injected into HPLC.

The kava-kava lactone-containing solution obtained from Example 7 contained kava-kava lactones at concentration of 10 mg/ml. The kava-kava lactone-containing solution obtained from Example 8 contained kava-kava lactones at concentration of 2.0 mg/ml.

What is claimed is:

1. A method of obtaining a kava-kava lactone-containing product comprising heating pulverized kava roots in an aqueous solution including a cyclodextrin-based solubilizing agent to extract kava-kava lactones from the pulverized kava roots.

2. The method of claim 1, wherein the cyclodextrin-based solubilizing agent is in $\alpha$, $\beta$, or $\gamma$ form.

3. The method of claim 2, wherein the cyclodextrin-based solubilizing agent is cyclodextrin, hydroxypropylcyclodextrin, hydroxyethylcyclodextrin, glucosylcyclodextrin, maltosylcyclodextrin, or maltotriosylcyclodextrin.

4. The method of claim 3, wherein the cyclodextrin-based solubilizing agent is hydroxypropylcyclodextrin.

5. The method of claim 1, wherein the aqueous solution contains about 0.1 to about 15 percent by weight of the cyclodextrin-based solubilizing agent relative to the total weight of the aqueous solution.

6. The method of claim 1, wherein the pulverized kava root in the aqueous solution is heated to about 50 to about 90° C.

7. The method of claim 1, wherein the cyclodextrin-based solubilizing agent is in $\beta$ form.

8. The method of claim 7, wherein the cyclodextrin-based solubilizing agent is cyclodextrin, hydroxypropylcyclodextrin, hydroxyethylcyclodextrin, glucosylcyclodextrin, maltosylcyclodextrin, or maltotriosylcyclodextrin.

9. The method of claim 8, wherein the cyclodextrin-based solubilizing agent is hydroxypropylcyclodextrin.

10. The method of claim 9, wherein the aqueous solution contains about 0.01 to about 25 percent by weight of the cyclodextrin-based solubilizing agent relative to the total weight of the aqueous solution.

11. The method of claim 10, wherein the aqueous solution contains about 0.1 to about 15 percent by weight of the cyclodextrin-based solubilizing agent relative to the total weight of the aqueous solution.

12. The method of claim 9, wherein the pulverized kava root in an aqueous solution is heated to about 50° C. to about 90°.

13. A method of obtaining a kava-kava lactone-containing product, the method comprising:

heating a crude kava-kava lactone-containing preparation in an aqueous solution including a cyclodextrin-based solubilizing agent to solubilize kava-kava lactones in the crude preparation and thereby produce an aqueous kava-kava lactone-containing solution; and removing flavokawains from the kava-kava lactone-containing solution.

14. The method of claim 13, wherein the cyclodextrin-based solubilizing agent is in α, β, or γ form.

15. The method of claim 14, wherein the cyclodextrin-based solubilizing agent is cyclodextrin, hydroxypropylcyclodextrin, hydroxyethylcyclodextrin, glucosylcyclodextrin, maltosylcyclodextrin, or maltotriosyl-cyclodextrin.

16. The method of claim 13, wherein the aqueous solution contains about 0.1 to about 15 percent by weight of the cyclodextrin-based solubilizing agent relative to the total weight of the aqueous solution.

17. The method of claim 13, wherein the crude kava-kava lactone-containing preparation in an aqueous solution is heated to about 50 to about 90° C.

18. The method of claim 13, wherein the cyclodextrin-based solubilizing agent is in a β form.

19. The method of claim 18, wherein the cyclodextrin-based solubilizing agent is cyclodextrin, hydroxypropylcyclodextrin, hydroxyethylcyclodextrin, glucosylcyclodextrin, maltosylcyclodextrin, or maltotriosyl-cyclodextrin.

20. The method of claim 19, wherein the cyclodextrin-based solubilizing agent is hydroxypropylcyclodextrin.

21. The method of claim 20, wherein the aqueous solution contains about 0.1 to about 15 percent by weight of the cyclodextrin-based solubilizing agent relative to the total weight of the aqueous solution.

22. The method of claim 20, wherein the crude kava-kava lactone-containing preparation in an aqueous solution is heated to about 50 to about 90° C.

23. The method of claim 13, wherein the flavokawains are removed by filtering the kava-kava lactone-containing solution.

* * * * *